United States Patent
Attila

(10) Patent No.: US 7,654,265 B2
(45) Date of Patent: Feb. 2, 2010

(54) CONDOM VALVE

(76) Inventor: Mady Attila, 1450 S. Kihei Rd., Suite G 104, Kihei, HI (US) 96753

( * ) Notice: Subject to any disclaimer, the term of this patent is extended or adjusted under 35 U.S.C. 154(b) by 157 days.

(21) Appl. No.: 11/868,132

(22) Filed: Oct. 5, 2007

(65) Prior Publication Data

US 2009/0090369 A1   Apr. 9, 2009

(51) Int. Cl.
*A61F 6/04* (2006.01)
(52) U.S. Cl. ...................... 128/844; 128/918
(58) Field of Classification Search .......... 128/844, 128/918, 842; 604/347–352
See application file for complete search history.

(56) References Cited

U.S. PATENT DOCUMENTS

| | | |
|---|---|---|
| 1,225,341 A | 5/1917 | Lederer |
| 3,495,589 A | 2/1970 | Clement |
| 3,536,066 A | 10/1970 | Ludwig |
| 4,004,591 A | 1/1977 | Freimark |
| 4,378,008 A | 3/1983 | Osbon, Sr. |
| 4,576,156 A | 3/1986 | Dyck et al. |
| 4,664,104 A | 5/1987 | Jaicks |
| 4,735,621 A | 4/1988 | Hessel |
| 4,808,174 A | 2/1989 | Sorkin |
| 4,817,593 A | 4/1989 | Taller et al. |
| 4,829,991 A | 5/1989 | Boeck |
| 4,855,169 A | 8/1989 | McGlothlin et al. |
| 4,869,723 A | 9/1989 | Harmon |
| 4,898,184 A | 2/1990 | Skurkovich et al. |
| 4,993,431 A | 2/1991 | Reddy |
| 4,993,433 A | 2/1991 | Reddy |
| 5,109,871 A | 5/1992 | Thornton |
| 5,112,900 A | 5/1992 | Buddenhagen et al. |
| 5,137,032 A | 8/1992 | Harmon |
| 5,331,974 A | 7/1994 | Sook |
| 5,333,621 A | 8/1994 | Denzer |
| 5,370,131 A | 12/1994 | Hess |
| 5,413,117 A | 5/1995 | Wills |
| 5,421,350 A | 6/1995 | Friedman |
| 5,437,286 A | 8/1995 | Stratton |
| 5,458,114 A | 10/1995 | Herr |
| 5,469,863 A | 11/1995 | Shah |
| 5,471,998 A | 12/1995 | Kuyumciyan |
| 5,513,654 A | 5/1996 | Delson |
| 5,549,120 A | 8/1996 | Persson et al. |
| 5,551,612 A | 9/1996 | Hochfeld |
| 5,601,092 A | 2/1997 | Miller et al. |
| 5,603,335 A | 2/1997 | McClenahan |
| 5,623,946 A | 4/1997 | Hessel |
| 5,640,973 A * | 6/1997 | Blinn .................. 128/844 |
| 5,651,374 A | 7/1997 | Wester |
| 5,662,214 A | 9/1997 | Wood |
| 5,715,839 A | 2/1998 | Strauss et al. |
| 5,803,085 A | 9/1998 | Asinovsky |
| 5,806,524 A | 9/1998 | Hernandez |
| 6,425,397 B1 | 7/2002 | Liehs |
| 6,536,438 B1 | 3/2003 | Kakonyi |
| 6,840,244 B2 | 1/2005 | Kemp |
| 2006/0137692 A1 | 6/2006 | Samuelsson |

* cited by examiner

*Primary Examiner*—Patricia Bianco
*Assistant Examiner*—James M Robinson

(57) ABSTRACT

A valve geometry applicable to the end of condoms to permit re-use with the same partner, or to enable condoms to permit the transmission of semen and thus permit conception as a result of intercourse while retaining the epidemiologically protective effect of barrier type infection control.

1 Claim, 5 Drawing Sheets

CONDOM VALVE

STATEMENT REGARDING FEDERALLY SPONSORED RESEARCH OR DEVELOPMENT

Not Applicable (No Federal Government Sponsorship or Involvement)

NAMES OF PARTIES TO A JOINT RESEARCH AGREEMENT

Not Applicable (No Joint Research Agreement in Effect)

INCORPORATION BY REFERENCE OF MATERIAL SUBMITTED ON A COMPACT DISK

Not Applicable (No Ancillary Electronic Data Appended)

TECHNICAL FIELD

Condom, contraception, disease prevention, health and personal hygiene and sexual devices.

BACKGROUND OF THE INVENTION

Sexually transmitted diseases (STDS) remain an unresolved scourge of humanity.

Some such diseases, such as the plague and Bartonellosis, are transmitted through vectors and are not amenable to barrier type protection. However, the best protection for all other known STDs remains the condom.

Condoms are currently constructed of primarily elastic artificial membranes applied to the penis. Most are made of latex, shipped rolled into a ring form and deployed by unrolling onto the penis. Considerable ingenuity is sometimes utilized in deploying these condoms in intimate settings. For this reason users have been very reluctant to adopt modifications. Many adhesive type modifications have been proposed, but they have failed to gain any acceptance. Most due to the fact that they are useless, rendering condoms into no more than a disposable foreign body to interfere with intercourse. The remaining ones have failed due to inconvenience of use.

Most modifications proposed by prior art are not only inconvenient, but impractical and in many instances dangerous. In any case, most proposed changes compromise condoms' function as a barrier type of protectant and contraceptive.

Nevertheless, improvement in condom technology is imperative. Condoms are a necessary evil at best and outright harmful in some situations. They are much less effective than the 93% contraceptive efficacy advertised. They are cynically promoted as effective against STDs, when in fact they are only reliably effective (if used perfectly) against one entity: syphilis.

Condoms work against syphilis because the causative organism, a spirochete known as *Treponema Pallidum*, is very fragile. In fact, *T. Pallidum* dies immediately once the bodily fluids carrying it dry out. *Treponema* are also relatively large in size. For this reason, any crude barrier that simply separates the non-infected party from the partner will serve as a protectant.

This is not the case with gonorrhea and Chlamydia. This is even less the case with viruses. In fact, condoms are completely useless for the prevention of the transmission of the herpes virus. Hepatitis B, hepatitis C and even HIV are only partially prevented with condoms.

All of the above is only assuming appropriate use. Breakage during use, combination with solvents and a wide range of creative sexual endeavors that sometimes strain belief invalidate any possible protective use of condoms.

Finally, none of the above have any relevance in the setting of omission of condom use. Condoms are uniformly detested. Women don't like it because they reduce the male's sexual ardor and males ostensibly dislike them because they "reduce sensation". This is probably a fictitious, as condoms' greatest nuisance lies in the compression to which they subject the penis. Sufficient compression to maintain the condom on the penis invariably interferes with erection, both lessening its intensity and duration. Condoms therefore have very low rates of usage.

Condoms nevertheless are the only reasonable alternative to mass prevention of STDs and birth control. They are reasonably effective if used adequately for a limited set of clinical scenarios, they do prevent conception and are so inexpensive that third world economies can afford them for their public health needs. Significant improvement in the state of the art without significant increase in cost is likely to result in a momentous impact in the prevalence of STDs.

Condoms as currently constructed do not permit the transmission of semen. This is for several reasons, not the least of which is that they are usually intended for contraception, along with protection from STDs. Provision of means to initiate conception would confuse the issue.

The second issue, however, is that condoms are not particularly effective for STD. It has not been worthwhile to date to consider using a condom for its efficacy in preventing disease especially in the setting of a desire to conceive. This possibility is proposed.

LEXICON

The condom of claim 1 is that cylindrical pliable membrane designed to be retained on the male sexual organ (penis, phallus) during sexual intercourse.

The apposed membrane applied to the inner adhesive surface of the condom of claim 1 is a membrane that does not adhere to (or adheres only very weakly) to the adhesive on the inner surface of the condom, is intended only for the packaging and deployment of the condom and is discarded after deployment of said condom For the purposes of this patent, the PROXIMAL end of the condom of claim 1 is defined as that end of the condom that would transmit the opening permitting application of the condom. This convention is in accordance with anatomical convention.

The DISTAL end of the condom shall therefore be defined as the reservoir tip, the valvular apparatus described in the separate but concurrent application, or whatever part of the condom that is applicable to the glans penis.

STD—Sexually Transmitted Disease, a disease transmissible through the act of sexual intercourse.

The term target shall refer to the penis.

The term glans shall refer to glans penis, the terminal segment of the penis.

BACKGROUND ART (condom background is included regarding a concurrent application, since it is envisioned that this condom valve technology would be utilized primarily with adhesive condoms).

Extensive prior art is provided to illustrate the state of condom technology and the practical range of executable devices (i.e.: materials technology, geometries, efficacy, etc.). While there are a myriad of prior patents prescribing some manner of adhesion, there none in either US or Worldwide patent literature referring to full length condoms with adhesive use along the entire length of the condom. Presumably this is because of difficulty of deployment.

Two prior US patents (U.S. Pat. Nos. 5,421,350 & 5,458,114) and one foreign patent (SE521418, USPTO PUB#US2006137692) prescribe a condom affixed to the end of the penis. Partial length condoms, particularly those suggested to cover only the glans penis, are useless (and hazardous) unless the recipient is a midget with an orifice of microscopic depth acted upon by a giant with a penis of unnatural dimensions. Unless each new condom is surgically affixed to the skin of the penis and/or unless a permanent glue such as methyl methylacrylate (CrazyGlue) is used to somehow weld the leading edge of the condom to the shaft, the free edge of the condom will roll off the penis, thus rendering it useless.

One prior patent (U.S. Pat. No. 6,536,438) proposes using an adhesive only proximally. This would again defeat the purpose of attempting to improve a condom, namely better adherence. The adhesive would have to be very strong and (since there would be high stress at the glued/non-glued interface), the condom would be MORE, not less likely to tear.

Several other patents are cited proposing various means of providing improved adherence without the use of adhesives (U.S. Pat. Nos. 5,513,654 & 5,715,839, WO0226174). Aside from the obvious flaw of trying to achieve something easily achieved with adhesives through ridiculously convoluted means, none of these embodiments are practical. The target is a tumescent organ that is subject to detumescence. Nothing but an adhesive would maintain close contact under such circumstances. Further, several of the cited means propose increased compression as a means of gaining better traction, increasing the probability of detumescence and thus reducing security rather than enhancing it.

One patent (U.S. Pat. No. 5,603,335) proposes an intraurethral condom. This is not only silly, but also dangerous. Prevention of conception is a distant secondary function of condoms, as condoms are notoriously unreliable in this regard. Inserting a condom into the urethra or a repeat basis is further guaranteed to result in trauma, thus causing emission of blood along with semen and increasing the odds of STD transmission.

The female anatomy hasn't escaped unscathed from attempts to protect it, either. U.S. Pat. No. 5,623,946 proposed an improved receptive geometry integrating a ring at the introitus. Aside from the lack of popularity of female condoms (nobody outside the homosexual community uses them), this arrangement increases the chances of a tear at the ring/condom interface.

Several patents are cited to illustrate the range of means to enhance the ease of condom deployment (U.S. Pat. Nos. 5,471,998, 5,549,120, 5,651,374 & 5,662,214). Without fail these proposals are convoluted, expensive and impractical. Indeed, no practical means of deployment has ever been proposed for an adhesive condom, much less one that not only rivals but actually surpasses current devices in terms of ease of use.

A single prior application (the aforementioned SE521418/ USPTO PUB#US2006137692) proposes to integrate a burst device to transmit semen through the tip of the condom. It is not practical and is likely to be traumatic and injurious. It is also likely to increase the incidence of transmission of STDs as compared to a standard condom (possibly even beyond that, since it is likely to traumatize the penis and cause bleeding).

SUMMARY OF THE INVENTION

A valve geometry applicable to the end of condoms to permit re-use with the same partner, or to enable condoms to permit the transmission of semen and thus permit conception as a result of intercourse, while retaining the epidemiologically protective characteristics of the condom.

DETAILED DESCRIPTION OF THE INVENTION

Figure 1:
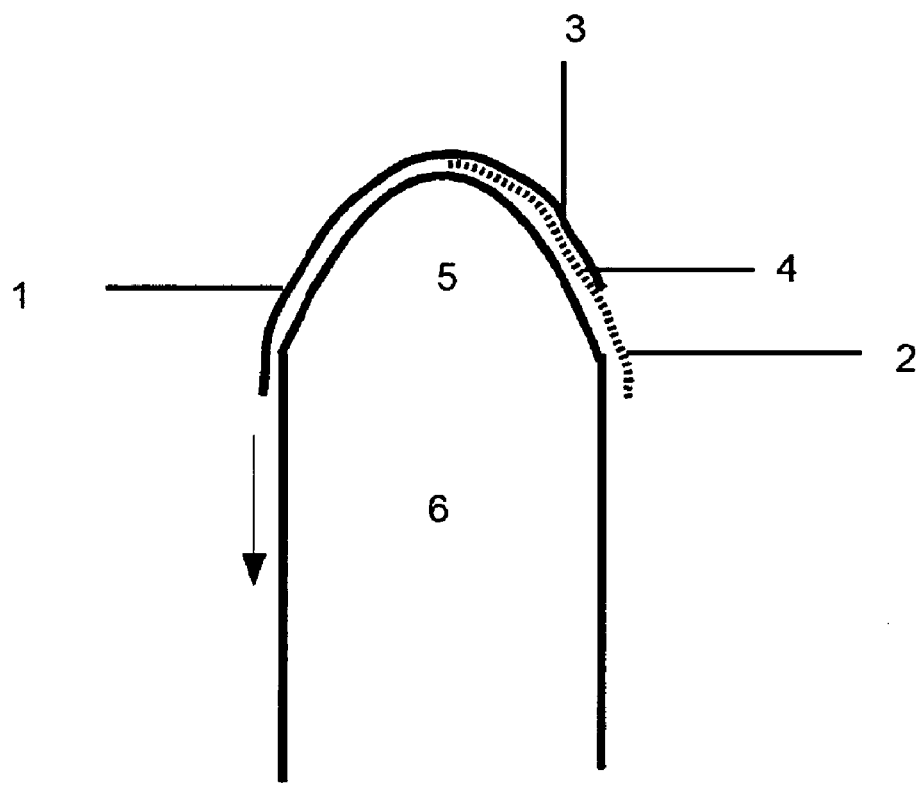
FIG. 1 (longitudinal view in cross section) shows the device as envisioned without a reservoir. Please note that the end of the condom is constructed in two layers which overlap and form a channel; the channel is open at the end, which permits egress of fluids under pressure (i.e.: ejaculation). Item 1 is the substance of the condom proper, Item 2 the inner layer of the condom plicated at this location, Item 3 is the outer layer of the condom plicated at this location, Item 4 the potential conduit defined by this doubling of layers, Item 5 the distal target (glans penis), item 6 the proximal target (shaft of penis).
Figure 2:
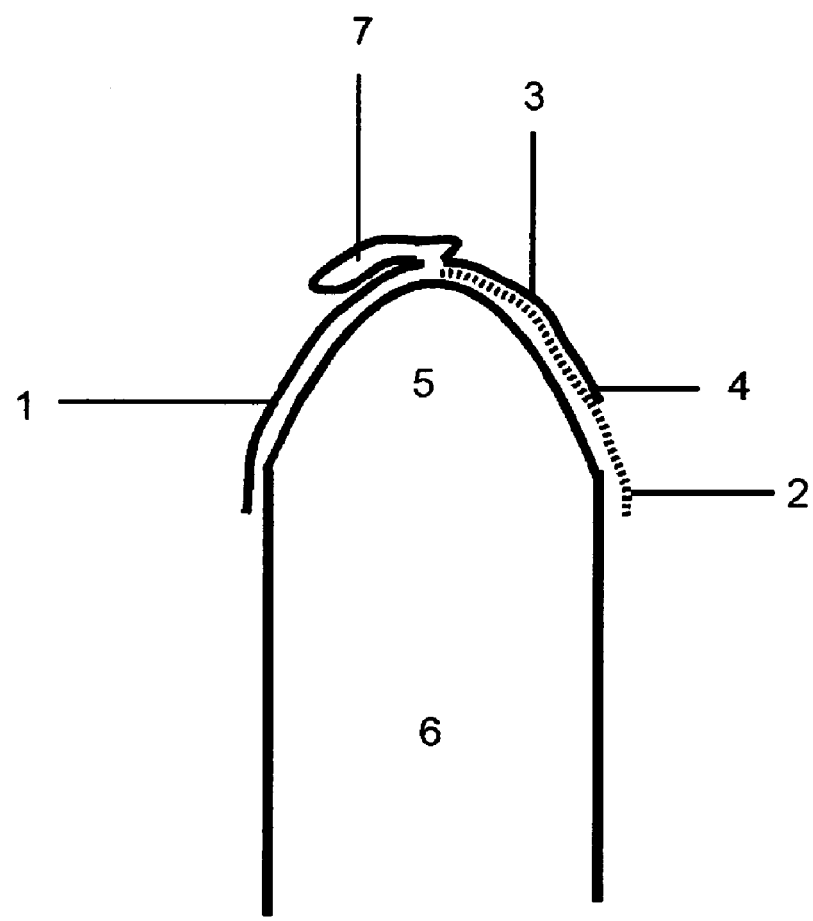
FIG. 2 ((longitudinal view in cross section) shows the device as envisioned with an unfilled reservoir. Same legend as FIG. 1, with additional Item 7 representing the empty reservoir.
Figure 3:
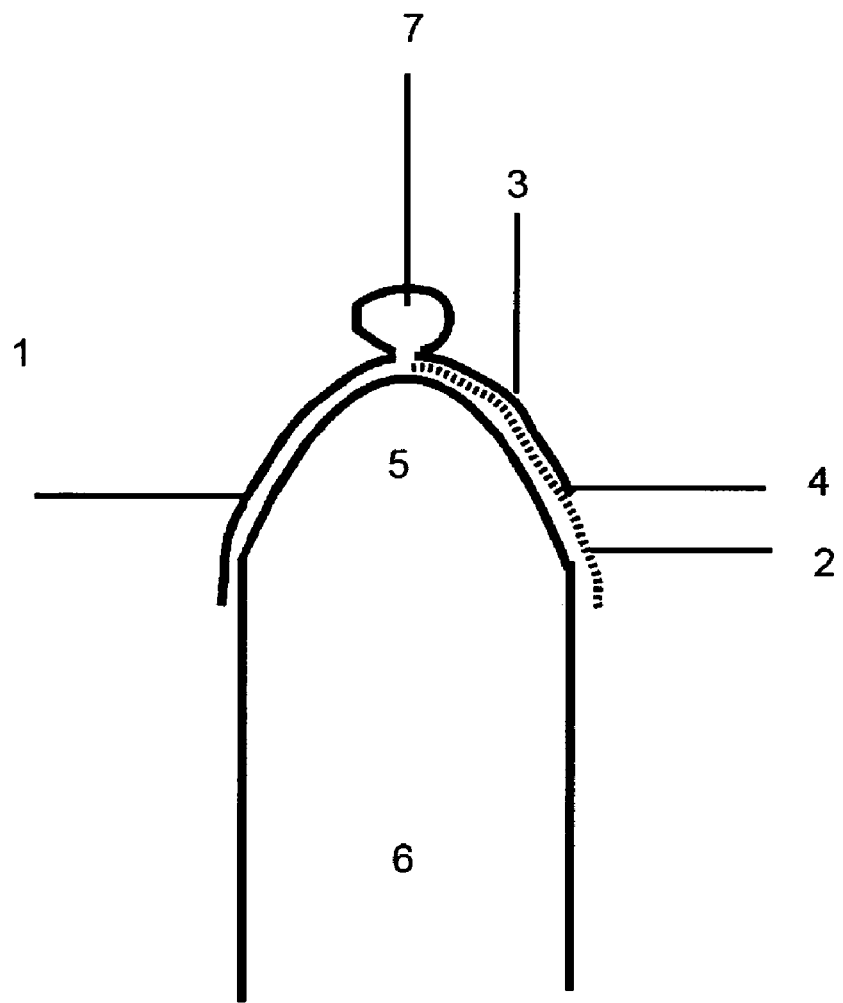
FIG. 3 ((longitudinal view in cross section) shows the device as envisioned with a filled reservoir. The reservoir is able to temporarily contain emissions and thus permit evacuation of contents at a chosen time. This permits reuse of the device, as emptying can occur between ejaculations at a time of choosing by the user. Same legend as FIGS. 1 and 2.
Figure 4:
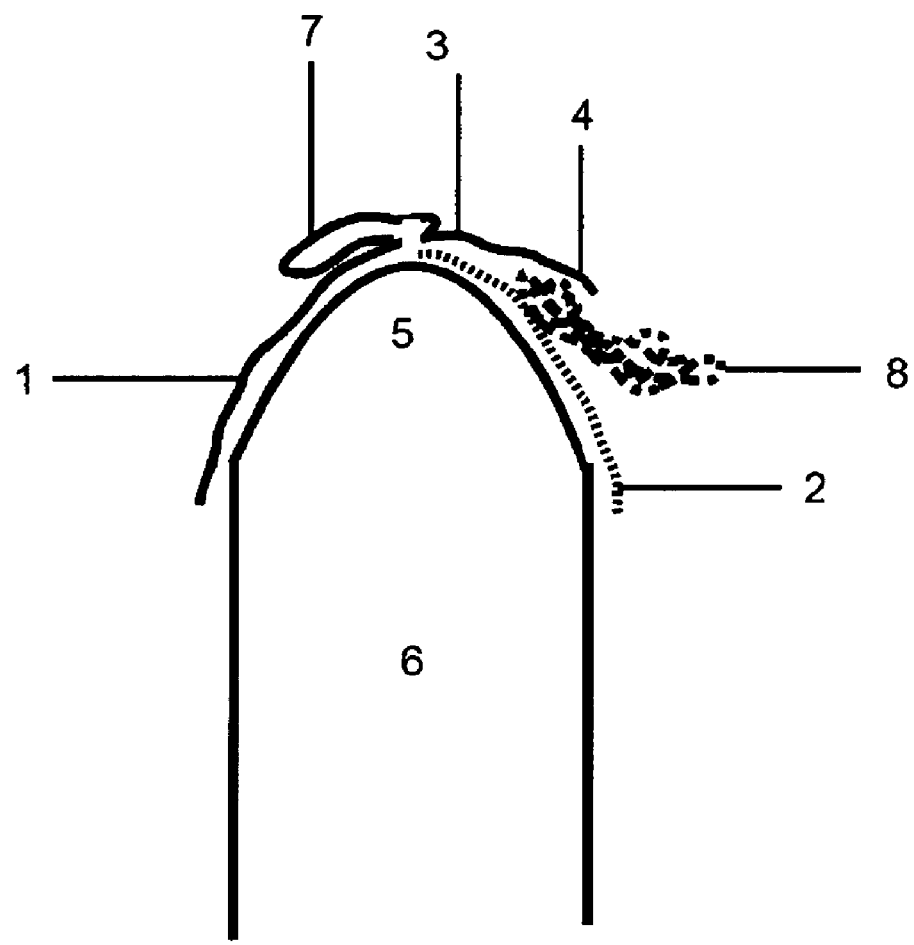
Figure 5:
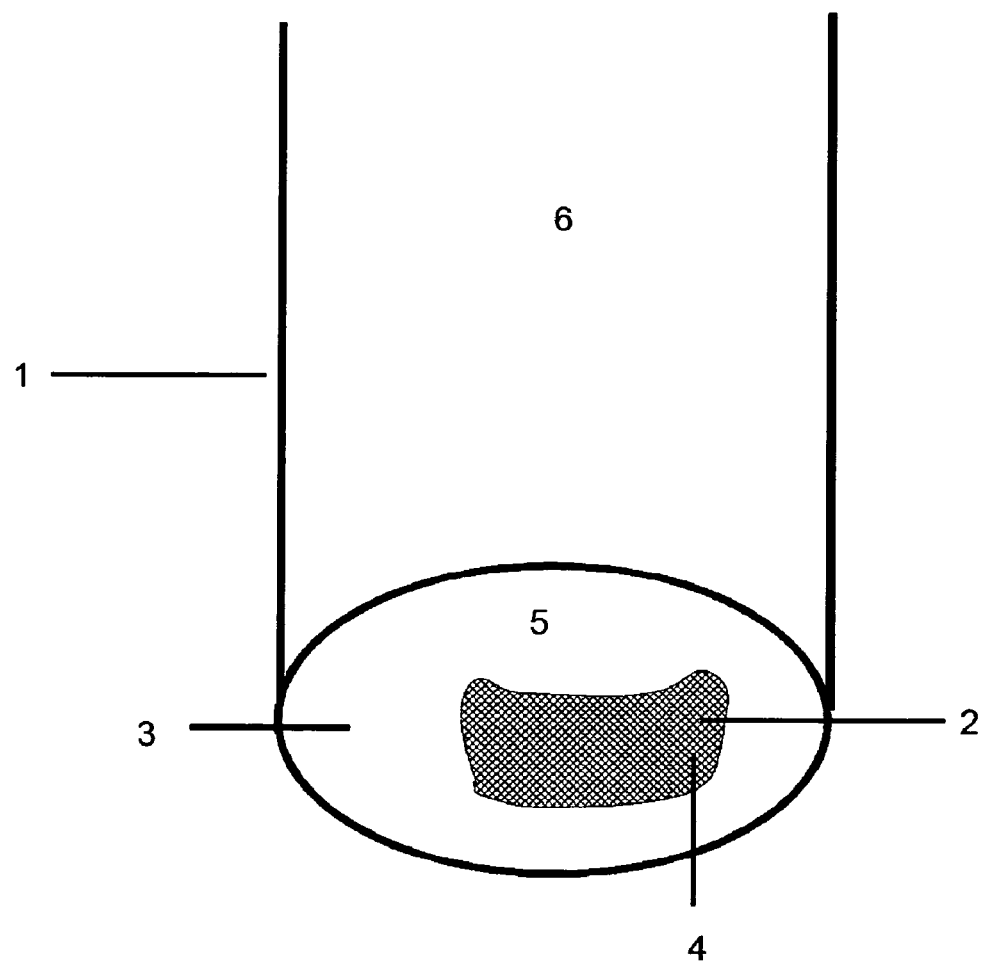

Condoms currently either integrate a reservoir at their end, or are finished to fit flush with the glans penis. A construction of overlapping membranes is envisioned for the distal (tip of glans penis) end of the condom that would be constructed in such a way that the more superficial layer of this construct would open under application of pressure and expose a conduit to permit to conduction of semen beyond the borders of the condom.

Specifically, two embodiments are envisioned. In the first the intent of the condom is to protect against STDs (or reflux of rectal contents), but permit conception. The two layers would be tightly apposed to the glans penis. The issuance of semen from the urethra would provide the pressure required to open the conduit and to transmit the ejaculate. Continued sexual activity would transmit the semen in a normal fashion into the female reproductive tract. Since the actual force of ejaculation has negligible effect on the transmission of semen through the cervical ostium, reproduction would not be affected.

The second embodiment envisions the use of a reservoir at the tip of the condom. The ejaculate would be retained as with current devices in the tip of the condom. However, a similar geometry to that described above would permit upon squeezing of this reservoir to expel the contents of this reservoir outside of the bounds of the condom. This would be particularly useful with the adhesive condom proposed in a separate and concurrent application and with proper cleaning of the condom and use of spermicide would permit the reutilization of an intact condom with the same partner. This way any inconvenience caused by the use of adhesives and irritation during exchange would be ameliorated.

The invention claimed is:

1. A condom having a valved geometry, said condom comprising a first layer and a second layer of a material that is capable of providing a barrier to the passage of bodily fluids, microorganisms and viruses, with said first layer and second layer configured in an overlapping fashion to form a plicated membrane valve at a distal portion of the condom, with said first and second layers further configured such that they are tightly apposed to the glans penis, with said condom further including a reservoir for retaining ejaculate at a distal tip of the condom, and wherein said plicated membrane valve is configured such that the aforesaid first and second layers may separate and the membrane valve may open under pressure provided from the urethra to transmit ejaculate therefrom, permitting emission of semen from the reservoir to an area outside of the confines of the condom in the region corresponding to and physically approximated to the introitus of the urethra, to prevent build-up of fluid at the tip of said condom and to permit impregnation of the female partner engaged in sexual intercourse.

* * * * *